United States Patent [19]
Quadro

[11] Patent Number: 5,244,897
[45] Date of Patent: Sep. 14, 1993

[54] GLYCYL-P-AMINO-PYRIDINE FOR THE TREATMENT OF SENILE DEMENTIA STATES

[75] Inventor: Giuseppe Quadro, Milano, Italy

[73] Assignee: Medea Research s.r.l., Milano, Italy

[21] Appl. No.: 853,780

[22] PCT Filed: Nov. 30, 1990

[86] PCT No.: PCT/EP90/02055
§ 371 Date: Jun. 2, 1992
§ 102(e) Date: Jun. 2, 1992

[87] PCT Pub. No.: WO91/07963
PCT Pub. Date: Jun. 13, 1991

[30] Foreign Application Priority Data
Dec. 4, 1989 [IT] Italy .................. 22595 A/89

[51] Int. Cl.$^5$ .......................... A61K 31/505
[52] U.S. Cl. .................................... 514/260
[58] Field of Search .......................... 514/260

*Primary Examiner*—S. J. Friedman
*Attorney, Agent, or Firm*—Buckman and Archer

[57] ABSTRACT

A pharmaceutical composition (orally or parenterally administered) containing glycyl-p-amino-pyridine monoacetate alone or together suitable carriers, which shows surprising anti-amnesic and anti-Alzheimer properties, is described.

4 Claims, No Drawings

GLYCYL-P-AMINO-PYRIDINE FOR THE TREATMENT OF SENILE DEMENTIA STATES

The present invention relates to the use of glycyl-p-amino-pyridine monoacetate of formula I

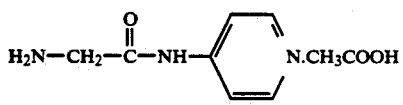

to prepare a medicament, which is particularly useful in the treatment of psychic and physical fatigue syndromes, memory disturbances, senile deficiency, psychoinvolution, nervous breakdown, and the like.

The present compound, hereinafter named with the code MR-3066, was disclosed in Indian Journal of Chemistry 5/524 1967 and in El. Naggar et al. J.Sci.-Res.1986 4 (2) (473/83 pag); in this last paper the antibacterial, disinfectant and antiseptic properties of various amino-acyl-amino-pyridines and amino-acyl-amino-pyrimidines are described.

It has now been found that the compound MR-3066 is endowed with anticonvulsivant properties, with effects on the cerebral acetylcholine release (without nevertheless showing Parkinson-like effect), with positive influence on learning and on amnesia episodes.

Therefore, the compound MR-3066 can be advantageously used in neurologic medicine for the treatment of symptoms and syndromes such as, for instance, the Alzheimer's disease (or senile dementia), for which no specific drugs exist so far. Aminopyridines affect the neurotransmitter release, by increasing it (Paskow et al., 1986) and at high dosages they induce convulsions.

Aminopyridines have been tested with favourable results in several clinical conditions ranging from diseases of neuromuscular transmission, including multiple sclerosis (Stefoski et al., 1987), to recovery from anaesthesia (Lechat et al., 1982; Pascow et al., 1986).

In Alzheimer's disease, the patient's cerebral cortex is remarkably damaged owing to neurohistological variations (neurofibrillar variations, etc), generally against temporal and frontal lobes, with resulting intellectual function deterioration; the initial clinical picture appears with psychogenic disorders, anxiety and depression, followed by confusion, memory disorders, reduced comprehension and judgement capacity, until to a total patient absence.

At the moment there is no effective therapy to treat this disease, which is considered to be irreversible.

The seriousness of the disease and its social impact justify clinical trials of rather toxic compounds, such as aminopyridines.

It has been pointed out the remarkable activity of the compound, if not for the resolution, at least for decreasing the syndrome.

TOXICOLOGIC AND PHARMACOLOGICAL EVALUATIONS

1) Acute toxicity

The acute toxicity of MR-3066 was evaluated after oral administration of the drug to the Swiss mice versus 4-aminopyridine.

The $LD_{50}$ was calculated according to the method described by Litchfield and Wilcoxon (J. Pharmacol. Exp. Ther. 96, 99; 1949).

TABLE 1

| Drug | Results $LD_{50}$ (mg/kg os) |
|---|---|
| MR-3066 | 29 |
| 4-aminopyridine | 12 |

The symptoms preceeding death were agitation, aggressiveness, jerks, stretchings and tonic convulsions.

MR-3066 showed a toxicity lower than 4-aminopiridine.

Acute convulsant activity

The acute convulsant activity of MR-3066 and 4-aminopyridine was compared in Swiss male mice after oral administration The $CD_{50}$ (Convulsant Doses 50) were calculated according to the method described by Litchfield and Wilcoxon (J. Pharmacol. Exp. Ther. 96, 99; 1949).

TABLE 2

| Drug | Results $CD_{50}$ (mg/kg os) |
|---|---|
| MR-3066 | 19 |
| 4-aminopyridine | 5 |

MR-3066 resulted less convulsant than 4-aminopyridine.

Toxicity after repeated administration—Preliminary study

The toxicity of MR-3066 after repeated administration was evaluated in male and female Sprague Dawley rat after oral administration of the drug (6 mg/kg) for 30 consecutive days.

Results

The oral administration of MR-3066 for 30 days to the rat brought no toxic phenomenon except for a slight decrease in body weight, increase in the female accompanied by a reduction in food consumption.

No sign of treatment related toxicity was either assessed from the hystopathological findings.

PHARMACOLOGY

Effect on acetylcholine release from the rat's cerebral cortex "in vivo"

1° study: Acute treatment

In this study the Acetylcholine release from the cerebral cortex was investigated in anesthetized rats (n=5) at different times before and after i.p. administration of MR-3066 at a dose of 5.6 mg/kg.

Results

The i.p. administration of MR-3066 at the dose of 5.6 mg/kg was followed by a marked increase in Ach release, which reached a peak after 45' and then gradually decreased.

At this dose no tremor or muscolar jerk were observed.

2° study: Chronic treatment

Three male rats receiving MR-3066 at the oral dose of 6 mg/kg for 30 consecutive days and then treated i.p. with 5.6 mg/kg of MR-3066, showed an increase in Ach. release similar to that observed in animals receiving the drug under study for the first time; accordingly, the repeated oral administration of MR-3066 induces no tachyphylaxis.

Learning behavior in normal mice (Passive avoidance response)

Male mice (body weight ca 20 grams) were used. The test apparatus was a box with a dark compartment and an illuminated one.

The animal was placed in the illuminated compartment, foot-shock was given immediately after the mouse moved in the dark compartement (acquisition trial).

MR-3066 was intraperitoneally administered immediately after the acquisition trial.

The test trial was carried out 24 h following the acquisition trial and the latency time to enter the dark compartment was recorded.

Results (Table 3)

MR-30-66 significantly prolonged the latency at the dose level of 5 mg/kg i.p.. The compound facilitated learning behavior in normal mice.

TABLE 3

Effect on the retention of passive avoidance response in mice (n = 20)

| Compound | Dose (mg/kg i.p.) | Mean latency (% of control) | Active dose (mg/kg i.p.) |
|---|---|---|---|
| MR-3066 | 0 | 100 | 5 |
| | 1 | 120.5 | |
| | 2.5 | 118.8 | |
| | 5 | 136.1** | |

Anti-amnesic activity was calculated according to the following formula: % of control = (the mean latency time of test compound treated mice/the mean latency time of vehicle treated mice) 100.
**P < 0.01 vs Control (0 mg/kg i.p.)

Effect on electroconvulsive shock—induced amnesia in mice

Male mice (body weight 23-26 grams) were used.

Test apparatus and passive avoidance training (acquisition trial) were as described in the previous section.

Immediately after acquisition trial, amnesia was induced by electroconsulsive shock (ECS).

Test compounds were administered intraperitoneally soon afterwards the exposure to ECS.

The test trial was performed 24 h after the acquisition trial: the animals were put in the illuminated compartment an the latency time to enter the unlighted compartment was recorded

Results (Table 4)

MR-3066 significantly prolonged the latency at the dose levels of 1 and 2.5 mg/kg i.p.. Physostigmine significantly prolonged the latency at the doses of 0.025 and 0.05 mg/kg i.p. and THA at the dose of 2.5 mg/kg i.p. MR-3066 showed an anti-amnesic effect more potently than THA did.

TABLE 4

Effect on electroconvulsive shock (ECS) induced amnesia in mice (n = 20)

| Compound | Dose (mg/kg i.p.) | Anti-amnesic activity (% of control) | Active dose (mg/kg i.p.) |
|---|---|---|---|
| MR-3066 | 0 | 100 | 1-2,5 |
| | 0,1 | 148,2 | |
| | 0,25 | 147,8 | |
| | 0,5 | 121,6 | |
| | 1 | 189,6** | |

TABLE 4-continued

Effect on electroconvulsive shock (ECS) induced amnesia in mice (n = 20)

| Compound | Dose (mg/kg i.p.) | Anti-amnesic activity (% of control) | Active dose (mg/kg i.p.) |
|---|---|---|---|
| | 2,5 | 165,5* | |
| | 5 | 148 | |
| Physostigmine | 0 | 100 | 0,025-0,05 |
| | 0,025 | 172,9* | |
| | 0,05 | 165,6* | |
| | 0,1 | 148 | |
| THA (tacrine) | 0 | 100 | 2,5 |
| | 0,5 | 72,2 | |
| | 1 | 114,4 | |
| | 2,5 | 184,5** | |

Anti-amnesic activity was calculated according to the following formula.
% of control = (the mean latency time of test compound treated mice/the mean latency time of vehicle treated mice) × 100.
*P < 0.05
**P < 0.01 vs control.

Effect on scopolamine—induced amnesia in mice

Test apparatus, mice and passive avoidance training (acquisition trial) were as described in the previous sections (4.2–4.3). The compounds were intraperitoneally administered 30 min. before the acquisition trial.

Amnesia was induced by scolopamine (1 mg/kg s.c.) given 20 min. prior to the acquisition trial; the test trial was performed after 24 hours.

The animals were put in the illuminated compartment and latency time to enter the dark compartment was recorded.

Results (Table 5)

MR-3066 significantly prolonged the latency at the dose level of 1 mg/kg i.p. and physostimgmine at the dose of 0.1 mg/kg i.p..

TABLE 5

Effect on scopolamine-induced amnesia in mice

| Compound | Dose (mg/kg i.p.) | Anti-amnesic activity (% of control) | Active dose (mg/kg i.p.) |
|---|---|---|---|
| MR-3066 | 0 | 100 | 1 |
| | 0,5 | 157,6 | |
| | 1 | 188,1** | |
| | 2,5 | 145,2 | |
| | 5 | 159,5 | |
| Physostigmine | 0 | 100 | 0,1 |
| | 0,025 | 119,5 | |
| | 0,05 | 134,5 | |
| | 0,1 | 155,5* | |

Anti-amnesic activity was calculated according to the following formula.
% of control = (the mean latency time of test compound treated mice/the mean latency time of vehicle treated mice) × 100.
*P < 0.05
**P < 0.01 vs Controls.

Spontaneous EEG in rabbits

Electrodes were chronically implanted in the motor cortex, the hippocampus and the nucleus amygdalae of rabbits (n=4).

The effects of compounds on spontaneous EEG were studied in the animals.

Results

MR-3066 (2 mg/kg i.v.) decreased fast wave activity in the motor cortex and increased theta activity in the hippocampus. The onset of the effects is five to 15 min. post administration, and their duration ranges from two to three hours.

Similar findings were observed immediately after the administration of physostigmine (0.1 mg/kg i.v.) and the effects lasted from 30 to 50 min.

MR-3066 showed effects similar to physostigmine, and the duration of action of the former compound is longer than that of the latter one.

Transcallosal evoked potential in rats

Electric stimulus was given to the callosum of urethane anesthetized rats, and transcallosal evoked potential from the opposite side cerebral cortex was measured.

The effects of the compounds on the transcallosal evoked potential were studied in rats.

Results

MR-3066 (2 mg/kg i.v.) and physostigmine (0.1 mg/kg i.v.) increased the amplitude of negative wave.

MR-3066 was found to be still more effective than physostigmine.

Both compounds raised the mean blood pressure, but the effect of physostigmine was much more marked than MR-3066.

The present invention refers to all the aspects which are industrially connected to the use of MR-3066 as active agent useful for the treatment of neurological and cerebral pathologies.

Therefore, one essential aspect of the invention is constituted by pharmaceutical compositions containing MR-3066 alone or in admixture with one or more pharmaceutically acceptable carriers, in the shape of tablets, sugar-coated pills, pellets, injectables.

The pharmaceutical compositions of the present invention are preferably administered in doses ranging from 1 to 500 mg according to the pathology, the sex, and the age.

The following example further illustrates the invention.

EXAMPLE 5 g (23.9 moles) of carbobenzoxy-glycine dissolved in tetrahydrofurane (150 ml) containing 1.9 ml of pyridine and 2.63 ml of N-methyl-morpholine, cooled to $-15°$ C. (ice/salt bath) are treated under stirring with 3.12 ml (21.9 moles) of isobutyl-chloroformate.

After 15 minutes 2.14 g of 4-amino-pyridine are added, and the reaction mixture is kept under stirring overnight at room temperature, then the solvent is evaporated under low pressure and the residue is recovered with ethyl acetate and water.

The organic phase is washed twice with a 1M sodium bicarbonate solution, then with water till neutral reaction, and dried on anhydrous sodium sulphate.

After solvent evaporation the residue is crystallized from ethyl acetate (hot/cold), filtered, washed with diethyl ether and vacuum-dried. 4.2 g (yield 66%) are obtained. M.P. 113°–116° C.

3.5 g of glycyl-p-amino-pyridine, dissolved in about 100 ml of methanol containing 10% of acetic acid, are hydrogenated for about 3 hours in the presence of Pd/C.

the catalyst is filtered on Celite and the filtrate is evaporated to dryness. The partially oily residue is recovered with diethyl ether and crystallizes spontaneously.

The product is filtered and vacuum-dried.

1.8 g (yield 53%) are obtained. M.P. 182°–184° C. (dec.).

| ELEMENTAL ANALYSIS | | | |
| --- | --- | --- | --- |
| | C | H | N |
| % calculated | 51,18 | 6,16 | 19,90 |
| % found | 51,49 | 6,31 | 19,89 |

NMR SPECTRA [Varian EM 390 −90 MHZ] ($D_2O$)

| CHEMICAL SHIFT | MOLTE-PLICITY | INTE-GRATION | ATTRIBUTION |
| --- | --- | --- | --- |
| 2.0 | singlet | 3H | $CH_3-COOH$ |
| 4.05 | singlet | 2H | $-\overset{\underset{\|}{O}}{C}-CH_2-N$ |
| 7.6 | doublet | 2H | pyridine ring (H positions) |
| 8.5 | doublet | 2H | pyridine ring (H positions) |

I claim:

1. The method of treatment of a living subject affected by senile dementia and Alzheimer disease syndromes, which consists of administering to said living subject orally or intraperitoneally or orally followed by intraperitoneal administration an effective amount of glycyl-p-amino pyridine, alone or in mixture with pharmaceutically acceptable carriers.

2. The method according to claim 1 wherein said glycl-p-amino pyridine is administered in the dose of 1–500 mgs.

3. The method according to claim 1 wherein said glycl-p-amino pyridine improves the release of acetylcholine in the brain of said living subject.

4. The method according to claim 1 wherein said syndromes of senile dementia and Alzheimer disease are memory loss, confusion and nervous breakdown and they are decreased by said treatment.

* * * * *